United States Patent
Williams et al.

(10) Patent No.: US 9,277,953 B2
(45) Date of Patent: Mar. 8, 2016

(54) ELECTROSURGICAL APPARATUS AND SYSTEM

(71) Applicant: GYRUS MEDICAL LIMITED, St. Mellons (GB)

(72) Inventors: Wayne Williams, Penarth (GB); Teo Heng Jimmy Yang, Cardiff (GB); Jack Dunkley, Bristol (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 435 days.

(21) Appl. No.: 13/573,672

(22) Filed: Oct. 3, 2012

(65) Prior Publication Data

US 2013/0090643 A1  Apr. 11, 2013

(30) Foreign Application Priority Data

Oct. 6, 2011 (GB) .................................. 1117273.1

(51) Int. Cl.
*A61B 18/04* (2006.01)

(52) U.S. Cl.
CPC .................................... *A61B 18/042* (2013.01)

(58) Field of Classification Search
CPC ............... A61B 18/042; A61B 18/14; A61B 2018/00589; A61B 2018/00166; A61B 2018/00202; A61B 2018/00583; A61B 17/3203; A61B 17/32035; A61B 2018/00017
USPC .............................................. 606/33, 40–52
See application file for complete search history.

(56) References Cited

U.S. PATENT DOCUMENTS

| | | | |
|---|---|---|---|
| 4,040,426 A | | 8/1977 | Morrison, Jr. |
| 4,898,574 A | * | 2/1990 | Uchiyama et al. ............. 604/22 |
| 5,330,422 A | * | 7/1994 | Schneider ...................... 604/27 |
| 5,720,745 A | * | 2/1998 | Farin et al. ...................... 606/49 |
| 5,730,752 A | * | 3/1998 | Alden et al. ...... A61B 17/32002 604/35 |
| 6,039,736 A | * | 3/2000 | Platt, Jr. ........................ 606/49 |
| 6,197,026 B1 | | 3/2001 | Farin et al. |
| 6,616,660 B1 | * | 9/2003 | Platt .............................. 606/49 |
| 7,727,225 B2 | * | 6/2010 | Broaddus et al. .............. 604/537 |
| 7,993,339 B2 | * | 8/2011 | Kuhner ............................ 606/49 |
| 8,460,283 B1 | * | 6/2013 | Laroussi et al. ................ 606/34 |
| 2004/0044342 A1 | * | 3/2004 | Mackay ........................ 606/45 |
| 2006/0025752 A1 | * | 2/2006 | Broaddus et al. ............. 604/537 |
| 2006/0036239 A1 | * | 2/2006 | Canady .......................... 606/49 |
| 2010/0114092 A1 | * | 5/2010 | Eisele et al. ................... 606/41 |

OTHER PUBLICATIONS

Search Report issued in British Application No. 1117273.1 dated Jan. 10, 2012.

* cited by examiner

*Primary Examiner* — Jaymi Della
(74) *Attorney, Agent, or Firm* — Oliff PLC

(57) ABSTRACT

An electrosurgical apparatus for coagulating tissue comprises an elongated tube (3) having a proximal end and a distal end, and constituting a conduit though which ionizable gas can be supplied to the distal end of the tube. The tube (3) includes one or more apertures (9) in the tube such that the ionizable gas is capable of exiting the tube in a plurality of different directions. The tube includes at least one electrode (4) for ionizing the ionizable gas exiting the one or more apertures, and a shield (11) associated to with the tube (3) and movable so as to obscure at least part of the one or more apertures (9) so as to vary the direction or directions in which the ionized gas exits the tube.

10 Claims, 5 Drawing Sheets

ELECTROSURGICAL APPARATUS AND SYSTEM

Figure 1:
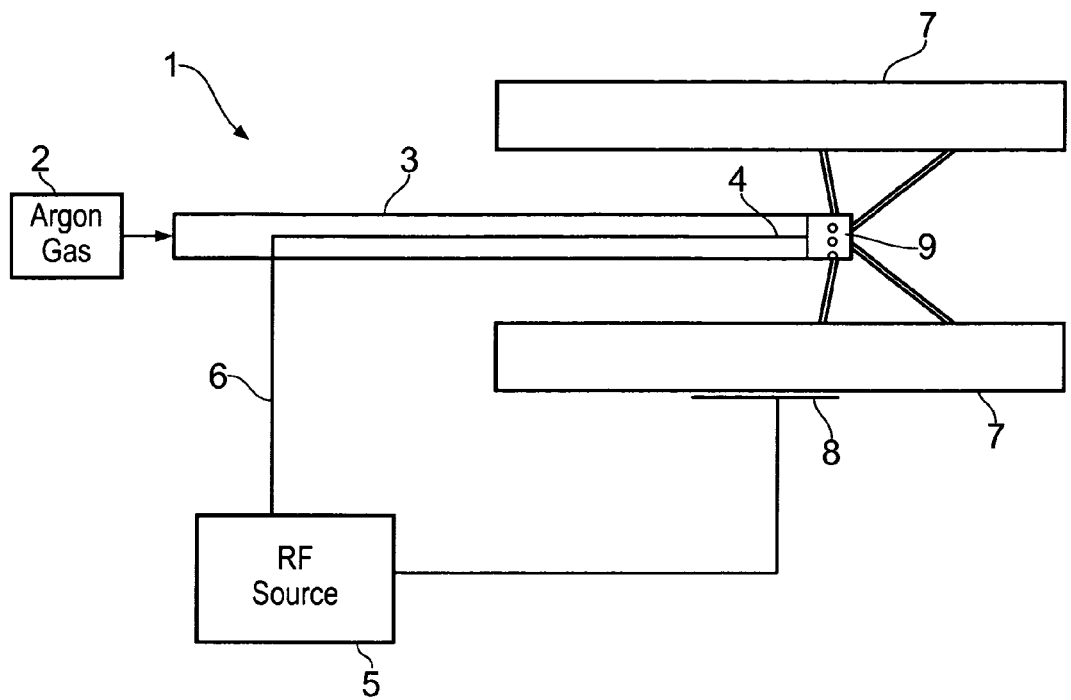

This invention relates to an electrosurgical apparatus and system and in particular to the non-contact coagulation of tissue using an ionisable gas such as argon. Argon beam coagulators have been known for many years, and examples are given in U.S. Pat. Nos. 4,040,426, 5,720,745, 6,039,736 and 6,197,026. The first example is an end-effect instrument, in which the ionised gas exits through the end of the instrument, while the latter two examples are directed at side-effect instruments, in which the ionised gas exits the instrument though an aperture in the side of the instrument. Such instruments are often referred to as APC instruments (Argon Plasma Coagulation).

The invention attempts to provide an instrument which is more versatile than any of the instruments in the prior art, and accordingly resides in an electrosurgical apparatus for coagulating tissue, comprising an elongated tube having a proximal end and a distal end, a conduit through which ionisable gas can be supplied to the distal end of the tube, the tube including one or more apertures in the tube such that the ionisable gas is capable of exiting the tube in a plurality of different directions, at least one electrode for ionising the ionisable gas exiting the one or more apertures, and a shield associated with the tube and movable so as to obscure at least part of the one or more apertures so as to vary the direction or directions in which the ionised gas exits the tube.

Previous APC instruments have had a fixed aperture or array of apertures, such that the operation of the instrument is unchangeable. The present invention provides a way of changing the operation of the instrument to obtain different tissue effects, from a single instrument. The shield is conveniently located within the tube, although it is conceivable that the shield may be located externally of the tube.

The tube preferably includes at least one aperture located around the circumference of the tube such that ionised gas is capable of exiting laterally with respect to the longitudinal axis of the tube. Typically, the tube includes a plurality of apertures located around the circumference of the tube such that ionised gas is capable of exiting in a plurality of different lateral directions. By moving the shield, the ionised gas can be selected to emerge from a chosen aperture, or a chosen range of apertures. In this way, the direction of the emerging gas can be controlled, such that the instrument can be selected to operate as a side-effect instrument in any chosen direction.

In one convenient arrangement, the tube includes an end face and at least one aperture in the end face such that ionised gas is capable of exiting longitudinally with respect to the longitudinal axis of the tube. The shield can preferably be moved so as cover either the at least one aperture in the end face, or the at least one aperture located around the circumference of the tube. By moving the shield in this way, the instrument can be selectively altered to act as either an end-effect instrument or as a side-effect instrument. Previous APC instruments have either been end-effect instruments or side-effect instruments, and individual surgeons have tended to prefer one type of instrument over another. This embodiment of the invention provides a hybrid APC instrument, which is capable of acting as either a side-effect or an end-effect instrument, depending on the position of the shield.

The shield conveniently comprises a member rotatably mounted with respect to the tube, different rotational positions of the member obscuring different combinations of the plurality of apertures. The member conveniently comprises an inner sleeve, the sleeve including one or more cut-out portions in the region of the apertures. By rotating the member, the sleeve can be maneuvered to obscure certain selected apertures, and to allow the cut out portions to leave open other selected apertures. Whether this involves changing the lateral direction of the emerging gas, or changing the direction of the gas between the side and the end of the instrument, the shield can alter the tissue effect obtained from the instrument without moving the instrument with respect to the tissue, or moving any external ports.

In an alternative arrangement, the tube includes one or more elongated apertures extending at least partly around the circumference of the tube. Once again, the shield comprises a member rotatably mounted with respect to the tube, different rotational positions of the member obscuring different portions of the one or more elongated apertures. Where there is a plurality of elongated apertures disposed around the circumference of the tube, the rotation of the member can select the aperture or apertures through which the ionised gas can exit.

Alternatively, the tube conceivably includes a single elongated aperture and the shield comprises a member rotatably mounted with respect to the tube, different rotational positions of the member obscuring different portions of the elongated aperture. In this arrangement, rather than obscuring different apertures, the shield obscures different sections of a single elongated aperture. The effect is similar, however, in that the direction of the emerging gas can be altered, not by diverting it to a different aperture, but by diverting it to a different part of an elongate slot. In similar fashion to the embodiments described with multiple apertures, the member conveniently comprises an inner sleeve, the sleeve including one or more cut-out portions in the region of the apertures. By moving the cut-out portions to open different sections of an elongate slot, the direction of the emerging gas can be controlled.

The present invention has the additional advantage that the amount of gas emerging from the tube is reduced. In other APC devices with multiple apertures, such as that disclosed in U.S. Pat. No. 5,720,745, ionisable gas will flow from all of the apertures, even though only a minority of apertures are being used to emit ionised gas. By shielding some of the apertures, less un-ionised gas will be emitted, saving on gas usage and reducing possible complications caused by un-ionised gas entering the patient.

The tube is conveniently flexible, such that it can be used in endoscopic surgical procedures, in which the tube is required to reach the intended surgical site via a lumen within the body of a patient. Alternatively, the tube may be rigid, in which case the instrument is more suitable for laparoscopic surgical procedures. The tube is conceivably a composite tube, with a body portion and an end-piece. The apertures may conveniently be present either in the body portion, the end-piece, or both.

In one arrangement, the apparatus includes only a single electrode for ionising the gas, the electrical circuit being completed via a patient return pad present on the patient. This form of instrument is commonly known as a monopolar instrument. Alternatively, the instrument may conveniently be a bipolar instrument, with first and second electrodes present on the instrument. In such a bipolar instrument, the electrodes are relatively close together, and the electrical circuit is completed by the electric current flowing from one electrode to the other, through the ionisable gas. Conceivably, the electrodes could be placed further apart, with the electrical circuit being completed capacitively.

The invention further resides in an electrosurgical system including an electrosurgical apparatus as described above, together with a source for supplying ionisable gas to the proximal end of said tube, and an electrosurgical generator for supplying high frequency energy to the at least one electrode. The electrosurgical generator is preferably adapted to supply the high frequency energy in the form of a succession of pulses. This means that a plasma arc formed in the ionisable gas is continually extinguished and re-established, resulting in a situation in which the re-established arc can take a different path should a different aperture now be available. Once an arc is established, the ionisation presents a low impedance path which may mean that the arc is maintained in its original path, even if an alternative path is now available. By constantly extinguishing and re-establishing the arc in this way, the arc will easily switch to different paths as the shield is repositioned, and the tendency for the arc to maintain a certain path beyond a desired duration is avoided.

While the shield has been described above with reference to changing the direction of the ionised gas, it can also be used to change the focus or spread of the ionised gas. Accordingly the invention further resides in an electrosurgical apparatus for coagulating tissue, comprising an elongated tube having a proximal end and a distal end, a conduit though which ionisable gas can be supplied to the distal end of the tube, the tube comprising at least one aperture located in the region of the distal end of the tube such that the ionisable gas is capable of exiting the tube through the at least one aperture, at least one electrode for ionising the ionisable gas exiting the at least one aperture, and a shield associated with the tube and movable so as to vary the size of the at least one aperture so as to adjust the spread of the ionised gas exiting the tube. Whether the at least one aperture is a circular aperture or an elongated slot, the movement of the shield can vary the size of the outlet. A relatively narrow outlet will produce a relatively narrow, focused beam of plasma, capable of relatively fine and detailed tissue coagulation. Conversely, a relatively large outlet will produce a relatively broad beam of plasma, capable of relatively large scale, bulk tissue coagulation. This aspect of the invention allows for the instrument to be changed between a fine tissue coagulator and a broad beam tissue coagulator, purely by the movement of the shield. Previously, two different APC instruments have been needed to be used in order to achieve both tissue effects.

Figure 2:
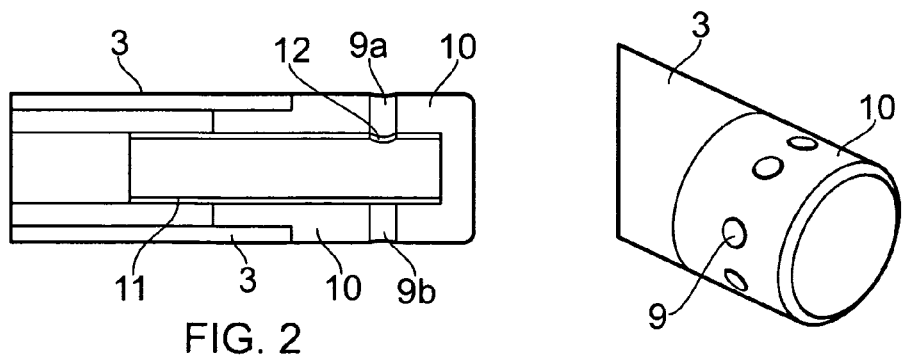
Figure 3:
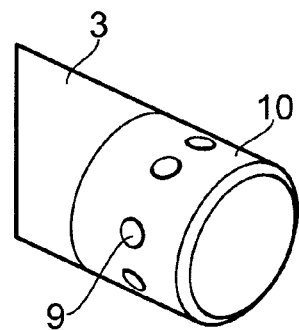
Figure 4:
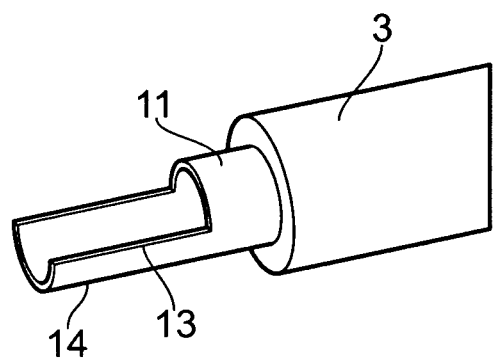
Figure 5:
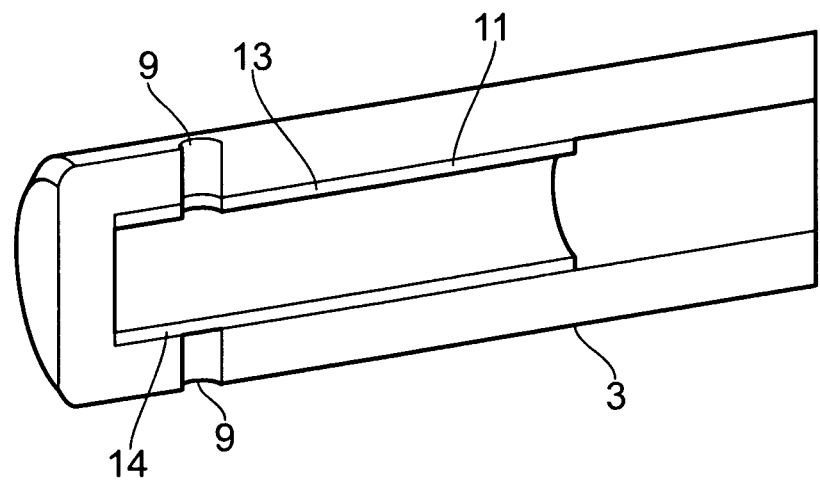
Figure 6:
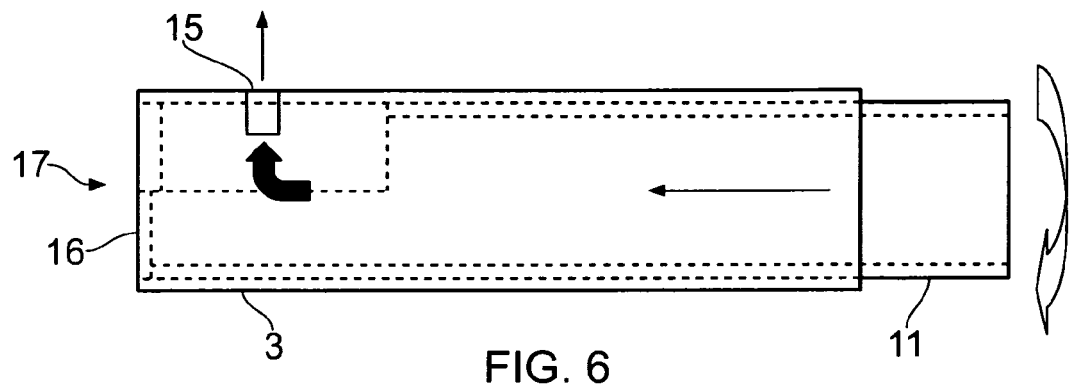
Figure 7:
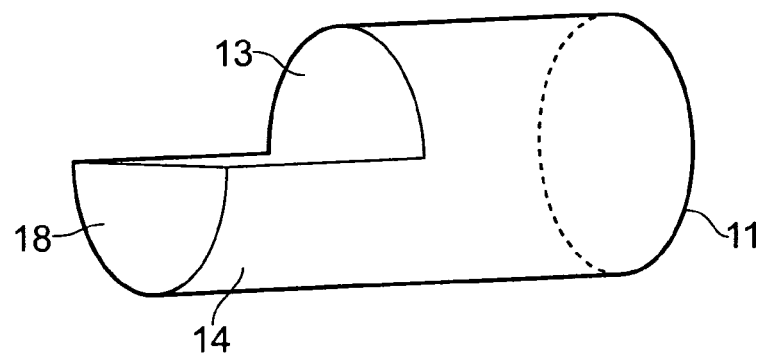
Figure 8:
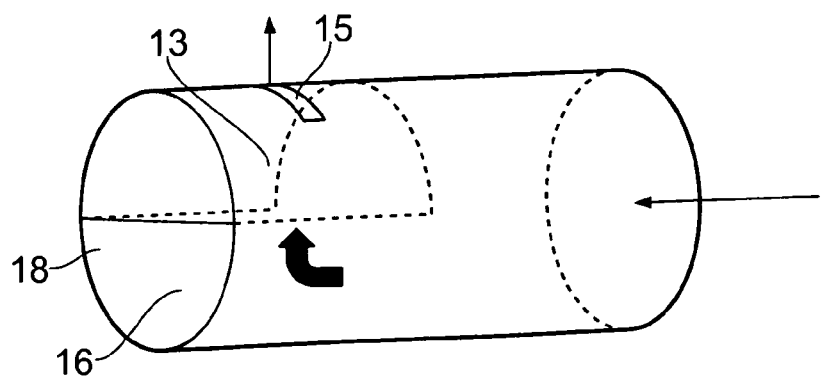
Figure 9:
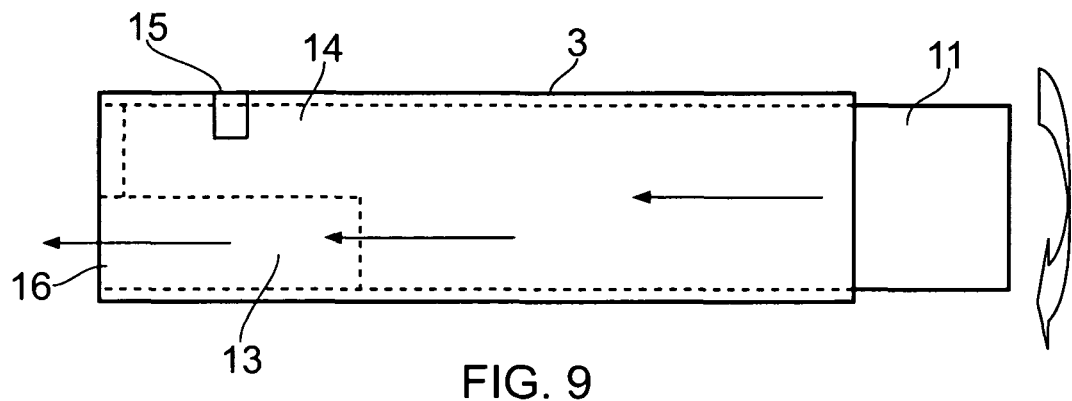
Figure 10:
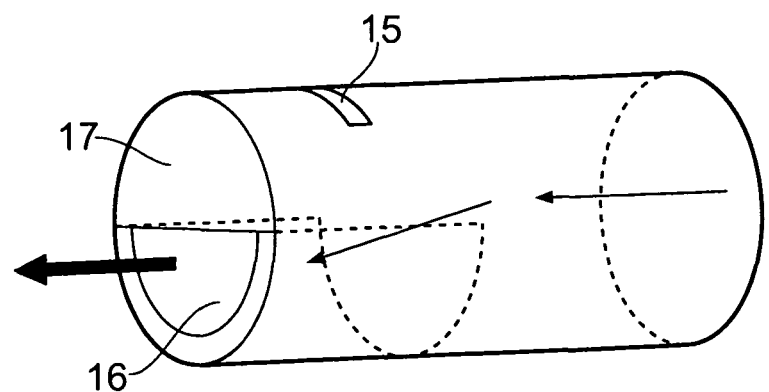
Figure 11:
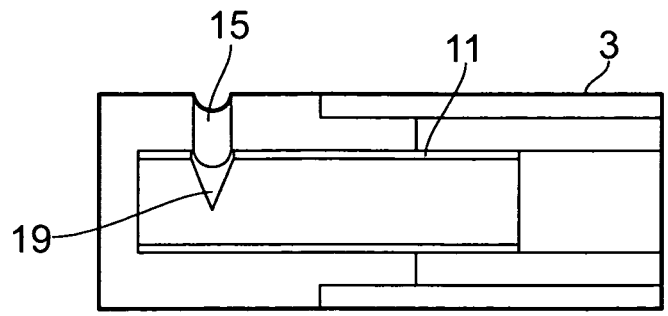
Figure 12:
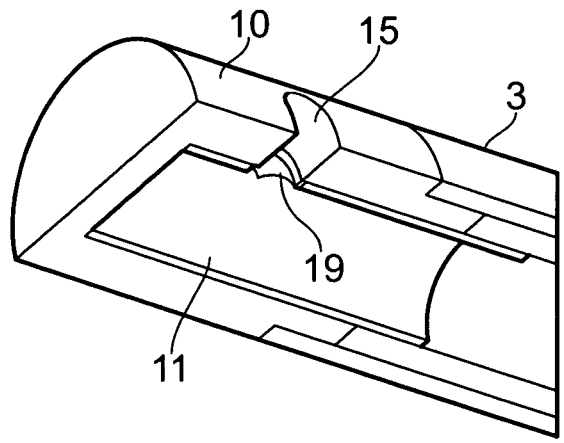
Figure 13:
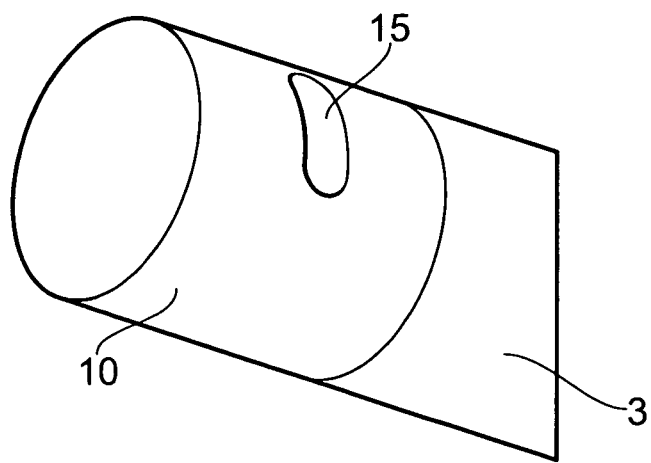

The invention will now be further described, by way of example only, with reference to the accompanying drawings, in which:

FIG. 1 is a schematic view of an electrosurgical system in accordance with the present invention, FIG. 2 is a schematic sectional view of the tip of an electrosurgical instrument used as part of the electrosurgical system of FIG. 1, FIG. 3 is a perspective view of the tip of an the electrosurgical instrument of FIG. 2, FIG. 4 is a schematic view, shown partly in section, of a part of an alternative electrosurgical instrument in accordance with the invention, FIG. 5 is a schematic sectional view of the electrosurgical instrument of FIG. 4, FIG. 6 is a schematic side view, showing hidden detail, of a part of another alternative electrosurgical instrument in accordance with the invention, FIG. 7 is a schematic perspective view of a part of the electrosurgical instrument of FIG. 6, FIG. 8 is a schematic perspective view, with hidden detail, of the electrosurgical instrument of FIG. 6, FIG. 9 is a schematic side view, showing hidden detail, of a part of the electrosurgical instrument of FIG. 6, shown in a second operational configuration, FIG. 10 is a schematic perspective view, with hidden detail, of the electrosurgical instrument of FIG. 6 in the second configuration;

FIG. 11 is a schematic sectional view of the tip of yet a further electrosurgical instrument in accordance with the invention, FIG. 12 is a cut-away perspective view of the tip of the electrosurgical instrument of FIG. 11, and FIG. 13 is an outside perspective view of the electrosurgical instrument tip of FIG. 11.

Referring to FIG. 1, an APC system comprises an instrument shown generally at 1, connected to a source 2 of argon gas. The instrument comprises a tube 3 containing an electrode 4, connected to a radio frequency generator 5 by means of cable 6. The instrument is shown schematically in position adjacent tissue 7, to which is connected a patient return pad 8, connecting the tissue to the generator 5. The tube 3 is provided with apertures, shown generally at 9, through which the argon gas can exit the tube. In use, the gas flows down the tube over the electrode 4, which causes the gas to ionise and form a plasma, which exits the apertures 9 and impinges on the tissue 7, thereby coagulating it.

FIGS. 2 and 3 show a first embodiment in which the user of the instrument can control which of the apertures 9 the argon gas can exit. The tube 3 is provided with a ceramic end-piece 10, in which the apertures 9 are formed. An inner sleeve 11 is positioned within the tube 3 and extends into the end-piece 10, the inner sleeve being provided with a single sleeve aperture 12. The sleeve is capable of being rotated by means of a handle (not shown) such that the sleeve aperture 12 can be aligned with any one of the apertures 9 in the end-piece 10. In use, the user rotates the sleeve 11 in order to align the sleeve aperture 12 with a first one of the apertures 9a, and argon gas is caused to flow from the source 2. The argon gas flows along the sleeve 11 and is converted into a plasma by means of the electrode 4 (omitted from FIG. 2 for the sake of clarity). The plasma then exits the aperture 9a and impinges on adjacent tissue, thereby coagulating it.

When the user wishes to coagulate tissue in a different orientation, the user rotates the sleeve 11 so that the sleeve aperture 12 is aligned with a different aperture 9b. Now the plasma will exit the aperture 9b, coagulating tissue adjacent thereto. In prior art instruments, the user would need to rotate the whole instrument 1 in order to achieve this effect, but in the instrument of FIG. 2, the user can achieve the same effect with only internal movement.

Referring to FIGS. 4 and 5, in an alternative embodiment the sleeve 11 is provided, not with a sleeve aperture 12, but with a cut-out 13 extending around 50% of the circumference of the sleeve. The cut-out 13 acts to allow argon gas to flow through the sleeve and out through those apertures adjacent the cut-out. Conversely, the part of the sleeve opposite the cut-out acts as a mask 14, and acts to block off those apertures 9 not adjacent the cut-out 13. In this way, the sleeve can be rotated in order to allow ionised gas to exit the instrument only through the apertures on one side of the instrument, and not through the apertures on the other side thereof. The cut-out 13 is shown in FIGS. 4 and 5 as extending around 50% of the circumference of the sleeve 11, but can alternatively extend around the circumference to a greater or lesser extent. For example, the cut-out can extend around only 90% of the circumference, in order to restrict the ionised gas to exiting in one quadrant only.

FIGS. 6 to 10 show a further alternative embodiment in which the tube 3 is provided with a side aperture in the form of a slot 15, and an end aperture 16 in the end face 17 of the tube 3. The end aperture 16 constitutes the lower semicircle of the end face 17, with the solid end face constituting the upper semicircle. The sleeve 11 is shown in FIG. 7, and comprises a cut-out 13 constituting 50% of the sleeve circumference, with the remaining 50% constituting a mask 14. The mask 14 also includes an end face 18, constituting a semicircle.

When the user wishes to operate the instrument 1 as a side-effect instrument, the user rotates the sleeve 11 so that it is in the position shown in FIGS. 6 and 8. In this position, the mask 14 is positioned such that semicircular end face 18 blocks the semicircular end aperture 16, preventing ionised gas from exiting the end of the instrument. However, the cut-out 13 is aligned with the slot 15, such that ionised gas can exit the slot and coagulate tissue adjacent thereto.

When the user wishes to operate the instrument as an end-effect instrument, the user rotates the sleeve 11 so that it is in the position shown in FIGS. 9 and 10. In this position, the mask 14 is positioned such that it blocks the slot 15, preventing ionised gas from exiting the side of the instrument. However, the cut-out 13 is aligned with the end aperture 16, such that ionised gas can exit the end of the instrument and coagulate tissue adjacent thereto. In this way, the user is able to change the instrument from a side-effect instrument to an end-effect instrument, merely by rotating the sleeve 11. There is accordingly no need to remove one instrument and replace it with another, in order to achieve this change in effect.

FIGS. 11 to 13 show yet a further alternative instrument in which the ceramic end-piece 10 is provided with a side slot 15, the slot being relatively elongate in nature. The inner sleeve is provided with a similarly sized slot 19, the two slots 15, 19 being of similar shapes. When the user wishes the instrument 1 to deliver a relatively broad beam of plasma to perform bulk tissue coagulation, the sleeve 11 is rotated such that the two slots 15, 19 are completely aligned. This allows the ionised gas to exit through the complete longitudinal extend of the elongate slot 15, resulting in a broad beam of plasma. Conversely, when the user wishes the instrument 1 to deliver a relatively narrow beam of plasma to perform fine tissue coagulation, the sleeve 11 is rotated such that the two slots 15, 19 are mis-aligned. By varying the amount of alignment of the slots 15, 19, the user is able to provide an effective exit aperture of different sizes, varying from the complete length of the slot 15 to a virtual pinhole (when the slots 15, 19 overlap by only the smallest of amounts). In this way, the user is able to vary the tissue effect caused by the instrument, and carry out both fine coagulation and bulk coagulation from the same instrument. Once again, the instrument can effectively act as two separate instruments, merely by effecting the rotation of an internal member.

Those skilled in the art will appreciate that other constructions can be envisaged without departing from the scope of the present invention. For example, instead of using a ceramic end-piece 10 as shown, the end-piece can be electrically conductive such that it constitutes the electrode 4. In this way, the plasma is initiated as it passes through the apertures, provided the distance to the tissue is small enough to maintain it. Other variations such as apertures of different shapes and sizes can be envisaged, as long as the basic idea of moving an internal member to adjust the apertures through which the ionised gas may exit the instrument.

The invention claimed is:

1. An electrosurgical apparatus for coagulating tissue, comprising:
    an elongated tube comprising:
        a proximal end;
        a distal end;
        a conduit through which ionisable gas can be supplied to the distal end of the elongated tube; and
        a gas outlet defined by at least one tube aperture in the elongated tube such that ionised gas is capable of exiting the elongated tube in a plurality of different directions,
    at least one electrode for ionising the ionisable gas to form the ionised gas capable of exiting the elongated tube; and
    a shield comprising an elongate inner sleeve rotatably mounted within the elongated tube, the elongate inner sleeve including at least one sleeve aperture formed within an outer circumferential surface of the elongate inner sleeve such that different rotational positions of the elongate inner sleeve obscure different parts of said gas outlet so as to vary a direction or directions of the plurality of different directions in which the ionised gas is capable of exiting the elongated tube,
        wherein the shield is asymmetric along a longitudinal axis of the shield.

2. The electrosurgical apparatus according to claim 1, wherein the at least one tube aperture is formed within an outer circumferential surface of the elongated tube such that the ionised gas is capable of exiting laterally with respect to a longitudinal axis of the elongated tube.

3. The electrosurgical apparatus according to claim 2, wherein,
    the at least one tube aperture comprises a plurality of tube apertures formed within the outer circumferential surface of the elongated tube such that the ionised gas is capable of exiting in the plurality of different directions, and
    the plurality of different directions comprises a plurality of different lateral directions.

4. The electrosurgical apparatus according to claim 2, wherein the at least one tube aperture comprises at least one radially extending aperture extending at least partly around the outer circumferential surface of the elongated tube.

5. The electrosurgical apparatus according to claim 1, wherein:
    the elongated tube includes an end face, and
    the at least one tube aperture is located in the end face such that the ionised gas is capable of exiting longitudinally with respect to a longitudinal axis of the elongated tube.

6. The electrosurgical apparatus according to claim 1, wherein the at least one sleeve aperture comprises at least one radially extending cut-out portion in a region of the gas outlet.

7. The electrosurgical apparatus according to claim 1, wherein:
    the at least one tube aperture comprises a plurality of tube apertures, and
    the different rotational positions of the elongate inner sleeve control a circumferential direction of the plurality of different directions in which the ionised gas is capable of exiting said gas outlet by obstructing some but not all of the plurality of tube apertures.

8. The electrosurgical apparatus according to claim 7, wherein the different rotational positions of the elongate inner sleeve control the circumferential direction in which the ionised gas is capable of exiting said gas outlet by fully obstructing some but not all of the plurality of tube apertures.

9. An electrosurgical system comprising:
    an electrosurgical apparatus comprising:
        an elongated tube comprising:
            a proximal end;
            a distal end;
            a conduit through which ionisable gas can be supplied to the distal end of the elongated tube; and a gas outlet defined by at least one tube aperture in the elongated tube such that ionised gas is capable of exiting the elongated tube in a plurality of different directions,
at least one electrode for ionising the ionisable gas to form the ionised gas capable of exiting the elongated tube; and
a shield comprising an elongate inner sleeve rotatably mounted within the elongated tube, the elongate inner sleeve including at least one sleeve aperture formed within an outer circumferential surface of the elongate inner sleeve such that different rotational positions of the elongate inner sleeve obscure different parts of said gas outlet so as to vary a direction or directions of the plurality of different directions in which the ionised gas is capable of exiting the elongated tube,
wherein the shield is asymmetric along a longitudinal axis of the shield;
a source for supplying the ionisable gas to the proximal end of said elongated tube; and
an electrosurgical generator for supplying high frequency energy to said at least one electrode.

10. The electrosurgical system according to claim 9, wherein the electrosurgical generator is adapted to supply the high frequency energy in the form of a succession of pulses.

* * * * *